United States Patent

Guglielmetti et al.

Patent Number: 5,139,707
Date of Patent: Aug. 18, 1992

[54] INDOLINO-SPIROQUINOXALINO OXAZINE PHOTOCHROMATIC COMPOUNDS, METHODS FOR THEIR PREPARATION, PHOTOCHROMIC COMPOSITIONS AND ARTICLES CONTAINING SUCH COMPOUNDS

[75] Inventors: Robert Guglielmetti; Pascale Tardieu, both of Marseille, France

[73] Assignee: Essilor International (Compagnie Generale d'Optique), Creteil, France

[21] Appl. No.: 532,326

[22] Filed: Jun. 5, 1990

[30] Foreign Application Priority Data

Jun. 5, 1989 [FR] France ............... 89 07401

[51] Int. Cl.⁵ .................. G02B 5/23; G03C 1/00; C07D 265/00
[52] U.S. Cl. .................... 252/586; 252/600; 544/71
[58] Field of Search .............. 252/582, 586, 600; 544/71

[56] References Cited

U.S. PATENT DOCUMENTS

| | | | |
|---|---|---|---|
| 4,637,698 | 1/1987 | Kwak et al. | 252/586 |
| 4,719,296 | 1/1988 | Irie et al. | 544/71 |
| 4,720,547 | 1/1988 | Kwak et al. | 252/586 |
| 4,931,220 | 6/1990 | Haynes et al. | 252/586 |
| 4,962,013 | 10/1990 | Tateoka et al. | 252/586 |
| 4,968,454 | 11/1990 | Crano et al. | 252/586 |
| 4,986,934 | 1/1991 | Kwiatkowski et al. | 252/586 |

FOREIGN PATENT DOCUMENTS 0245020 11/1987 European Pat. Off.
0313941 5/1989 European Pat. Off.

*Primary Examiner*—Robert L. Stoll
*Assistant Examiner*—Philip Tucker
*Attorney, Agent, or Firm*—Millen, White & Zelano

[57] ABSTRACT

The new photochromic compounds of the invention have the formula of a indolino-spiro-oxazine comprising an indolinic part and an oxazine part wherein the oxanine part comprises an unsaturated 6-atoms bi-aza heterocycle of the pyrimidine type included in a nucleus of the quinazoline part.

Preferred photochromic compounds are those showing the following developed formula (II) wherein
$R_1$ is a methyl or isopropyl group
$R_2$ and $R_3$ are methyl groups
$R_4$ is H or $-OCH_3$

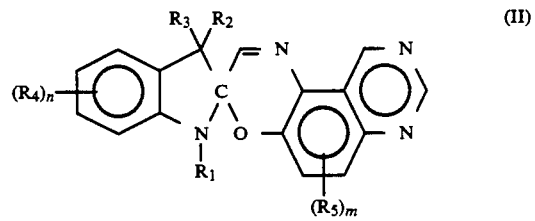

19 Claims, No Drawings

INDOLINO-SPIROQUINOXALINO OXAZINE PHOTOCHROMATIC COMPOUNDS, METHODS FOR THEIR PREPARATION, PHOTOCHROMIC COMPOSITIONS AND ARTICLES CONTAINING SUCH COMPOUNDS

The present invention concerns new photochromic compounds of the indolino-spiro-oxazine type, a method for their preparation, as well as compositions and articles with photochromic properties containing at least one of said photochromic coumpounds. Generally speaking, the compounds of the present invention can be used advantageously in making all sorts of optical lenses, the term optical lens including notably referring to an ophtalmic lens, a contact lens, or a sun protection lens.

Photochromism is a well known reversible phenomenom which is illustrated typically by a compound which undergoes a change in color when exposed to light radiations, including those in the U. V. range, such as sunlight, and returns to its original color upon stopping light exposure.

Such compounds are useful for example in the manufacture of lenses for sunlight-protection glasses or in other applications involving the need to vary the transparency of an article according to surrounding light intensity. They can be applied onto a transparent support or incorporated within a transparent polymerized organic material, in combination with a large variety of polymer compositions.

A number of organic photochromic compounds having a formula including an indolino-spiro-oxazine group have already been provided. They have encountered variable success in practice.

U.S. Pat. Nos. 3,562,172 and 3,578,602 have thus disclosed compounds showing a photochromic effect which belong to the family of indolino-spiro-naphtoxazines, while U.S. Pat. No. 4,215,010 describes indolino-spiro-naphtoxazines wherein the naphtalene nucleus comprises methoxy, ethoxy or halogen substituents.

Similar photochromic compounds comprising a pyridobenzene nucleus in place of the naphtalene nucleus of the above compounds are described in U.S. Pat. No. 4,720,547, as well as in the PCT specification No. 87/00524. The latter gives for such compounds a general formula involving in the oxazine part a hetero-aromatic group comprising one or two nitrogen atoms within two or three nuclei according to a general formula such as follows:

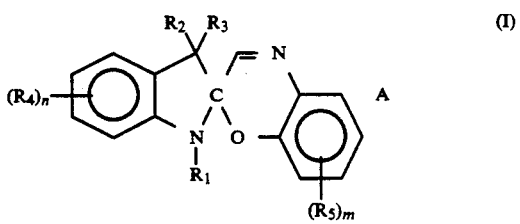

(I)

in which cycle A is an hetero-aromatic cycle comprising one or two nitrogen atoms.

However the only specific compounds that have been prepared and tested according to said patent specification comprise as the hetero-aromatic group a pyridobenzene, benzopyridobenzene or dipyridobenzene group.

The invention affords improvements to this type of photochromic compounds by enhancing the properties which are desired in their most frequent uses, especially as regards the compatibility with organic materials used in transparent lenses for sunlight protection and retention of the color desired when exposed to light for a long time.

With this aim, the invention provides new photochromic compounds especially selected within the general formulae above. They are characterized in that they show the formula of a indolino-spiro-oxazine comprising an indolinic part and an oxazine part wherein the oxanine part comprises a unsaturated 6-atoms bi-aza heterocycle of the pyrimidine type included in a nucleus of the quinazoline part.

The various cycles of the indoline and oxazine parts may carry various substituents that do not affect the global photochromic properties of the compounds.

More specifically, the new compounds according to the invention are represented preferably by the following developed formula:

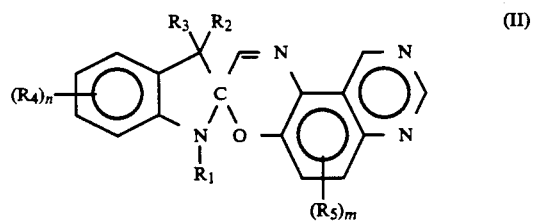

(II)

n varies from 0 to 4,
m can take values 1 or 2,
$R_1$ represents:
i) an alkyl group comprising from 1 to 16 carbon atoms such as a methyl, ethyl, n-propyl, isopropyl, n-butyl group;
ii) an allyl, phenyl, arylalkyl group such as a benzyl, phenyl mono or di-substituted by substituents such as alkyl or alkoxy having 1 to 6 carbon atoms;
iii) an alicyclic group such as a cyclohexyl group optionally substituted;
iv) an aliphatic hydrocarbon group comprising in its chain on or several heteroatoms such as O, N or S, especially an acid, ester or alcohol function;

$R_2$ and $R_3$ may each independently represent a $C_1$–$C_8$ alkyl, phenyl, mono or di-substituted phenyl group with substituents selected from $C_{1-4}$ alkyl and/or $C_{1-5}$ alkoxy groups, or may be comgined to form a cyclic ring with 6 to 8 carbon atoms (including the 3 spirannic carbon of the indolinic heterocycle);

$R_4$ and $R_5$ may each independantly represent:
i) an hydrogen atom, an amin function NR'R", wherein R' and R" each independantly represent an hydrogen atom, a group alkyl, cycloalkyl, phenyl, or a substituted derivative thereof; R' and R" may be combined into a cycloalkyl group that can be substituted or comprise one or several heteroatoms;
ii) a group R, OR, SR, COR or COOR wherein R represents a hydrogen atom, an alkyl group with from 1 to 6 carbon atoms, or an aryl or heteroaryl group;
iii) an halogen atom, a $C_{1-4}$ monohaloalkyl or $C_{1-4}$ polyhaloalkyl group such as $CF_3$, the halogen being typically Cl, Br;
iv) —$NO_2$, CN, SCN;

wherein each $R_4$ substituent can be present on anyone or the convenient carbon atoms in the indolin part of the photochromic compound, in 4, 5, 6, 7 positions, when the other one is a hydrogen atom, whereas when n=2 it is prefered that the substituents be present in positions 4 and 5, 5 and 6, 4 and 6 or 6 and 7.

Preferably:

$R_1$ is a $C_{1-4}$ alkyl, phenyl or benzyl group;

$R_2$ and $R_3$ are selected from the $C_{1-5}$ alkyl groups such as methyl and ethyl, or the phenyl group, or are combined to form a cyclohexyl group;

each of the $R_4$ groups is selected from the group comprising hydrogen, $C_{1-2}$ alkyl, chlorine, fluorine, bromine, iodine, $C_{1-2}$ tri-haloalkyl and $C_{1-5}$ alkoxy;

and $R_5$ is a hydrogen atom, or a $C_{1-4}$ alkoxy group, or a tertiary amine, or an halogen.

Of particular interest among the compounds of the invention are those wherein:

the oxazine part is of the pyrimidobenzene type;

$R_1$ is a $C_{1-4}$ alkyl group such as methyl, ethyl, isopropyl or n-butyl;

$R_2$ and $R_3$ each independently represent a methyl, ethyl, or phenyl group;

$R_4$ is a hydrogen atom, a methyl, methoxy or chloro group;

and $R_5$ is a hydrogen atom.

Another object of the present invention is a method for preparing the photochromic indolino-spiro-oxazine compounds represented by formula (II).

For one part it implements a general scheme for synthesizing heterocycles of type I which consists in performing the condensation of a Fischer base or 2-alkyliden indolinic compound with a hydroxy-nitroso-hetero-aromatic compound. However the intermediate hetero-aromatic compounds required to lead to the compounds of the invention are new in themselves and they have never been synthesized up to now.

According to the invention the suitable quinazoline compounds may be prepared from a 3-hydroxy benzaldehyde compound, optionally substituted with one or several $R_5$ radicals such as indicated for formula II, through a method comprising nitrating this compound, reacting the 3-hydroxy 6-nitro benzaldehyde obtained with formamide to obtain the corresponding benzyliden-bisformamide derivate, transforming the latter into 6-hydroxy-quinazoline and nitrosating this last compound.

When using them for preparing photochromic compositions, the compounds according to the present invention can be dissolved into a suitable solvent such as toluene or ethanol so as to obtain a photochromic solution. The same photochromic compounds can also be dissolved within a polymer, a copolymer or a mixture of polymers dissolved in a suitable organic solvent.

They are thereby incorporated in compositions according to the present invention which can be applied on, or introduced in, a transparent organic polymer material so as to obtain a photochromic transparent article. Preferably this material is a material of optical quality, and more particularly a material suitable for manufacturing ophtalmic lenses.

They can also enter into photochromic compositions which stand equally within the scope of the present invention and which can be used directly for constituting photochromic plastic films, boards or lenses such as lenses for sun glasses, sight finders, camera optics, and filters.

Examples of compositions which are suitable according to the invention for manufacturing photochromic transparent materials and articles, comprise one or several photochromic compounds according to the invention in combination with one or several of the following polymers: polymers from polyolallylcarbonate monomers, polyacrylates, polyalkyl-acrylates such as polymethyl methacrylate (PMMA), cellulose acetate, cellulose triacetate, cellulose propiono or butyro-acetate, polyvinyl acetate, polyvinyl alcohol, polyurethanes, polycarbonates, polyethylene-terephthalate, polystyrene, copolymers of styrene and methyl-methacrylate, acrylonitrile, polyvinylbutyral.

The amount of the photochromic compound (or the composition containing this compound) applied on, or introduced in the polymer material has no critical significance, and it depends generally from the desired color intensity under radiation and from the method used to incorporate and/or apply the photochromic compounds. This method can be anyone within the high number of methods convenient for photochromic compounds known from the prior art, and among them typically the dissolution, or dispersion of the compound in the basic composition of the material, or the application of a photochromic layer on the surface of or inside a transparent support material.

Generally speaking, higher is the amount of photochromic compound added, more important is the coloration under radiation. Such an amount can be described as a photochromic amount. Usually the amount of photochromic compound incorporated in the optical material is from 0.01 to 20% by weight, and preferably from 0.05 to 10% by weight, with respect to the total weight of the optical material.

Through the photochromic effects obtained thereby, there appears a coloration under exposure to radiations within the U.V range, with the original color or transparency being recovered when the exposure to U.V. radiations is interrupted. This change in coloration can be renewed a high number of times, in accordance with what is required for sunlight protection lenses. Furthermore the coloration remains all the time the material is exposed to sun radiations better than in the case of the photochromic compounds according to the prior art.

The invention will now be further illustrated by particular implementing examples which are not limitating.

EXAMPLE 1

Phasis 1

Being recalled that one knows how to prepare indolino-spiro-oxazines of formula I, for example from a 2-methylen indolinic compound and a 5-nitroso 6-hydroxy hetero-atomic compound, there is described in this first step the preparation of an intermediate compound of the 5-nitroso 6-hydroxy quinazoline type according to reaction A below, wherein $R_5$ has the same signification as in formula II for the photochromic compounds of the invention:

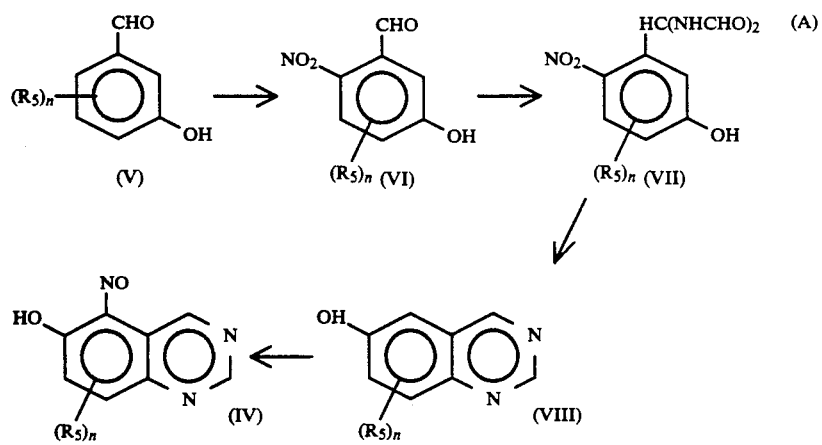

The starting compound has formula V wherein $R_5$ is H in this particular example.

3 g of 3-hydroxy benzaldehyde (formula V) are slowly added to 30 ml of nitric acid (d=1.17, 28% solution). The temperature of the solution is maintained between 35° C. and 45° C. At the end of the addition, hydrolysis is performed and the reaction mixture is then allowed to stand at room temperature. A yellow precipitate is so obtained; it is filtered and then refluxed in benzene (20 ml) during 15 to 20 minutes. The insoluble part is taken off and recrystallized in water. The 3-hydroxy 6-nitro benzaldehyde (formula VI) is recovered with a final yield of 25%.

M.P. =167° C. ($C_7 H_5 N O_4$, M=167).

In the next step, HCl gas is strongly bubbled in a mixture of 4 g of 3-hydroxy 6-nitro benzaldehyde and 30 ml of formamide. When the temperature reaches 100° C., the gas bubbling is stopped and the solution is allowed to stand at room temperature overnight. The solid is washed with ether, then placed in 10 ml of icewater and the pH is adjusted to 3 with 6N NaOH. The crude product is purified by recrystallization in water.

Yield 84%, M.P. =244° C. ($C_9 H_9 N_3 O_5$, M=239).

To a mixture of 2 g of the 3-hydroxy 6-nitrobenzylidene bis-formamide thus obtained (formula VII) with zinc dust (6 g) and crushed ice (24 g), 8 ml of acetic acid are added under stirring during 5 minutes. Stirring is continued at room temperature for 30 minutes (the temperature rises to 41° C.), then for 2 hours further while futher adding zinc (3 g) during the first hour. The solution is filtered, then extracted gently with ether oxide (pH=7-8). After evaporation of ether, the pH is adjusted to 5 with a 3N NaOH solution. The brown solid recovered (6-hydroxy quinazoline, formula VIII) is recrystallized in water.

Yield 57%, M.P.=239° C. ($C_8H_6N_2$, M=146).

During one hour and while stirring, a solution of 0.14 mole of sodium nitrite in 30 ml water is added to a cold solution (0°-5° C.) of 0.14 mole of 6-hydroxy quinazolin, 12 ml concentrated hydrochloric acid and 50 ml distilled water. Stirring is continued for one hour. The 5-nitroso 6-hydroxy quinazolin (formula IV) is thus obtained as a yellow precipitate, which is washed with water, then dried.

Yield 60%, M.P. =172° C. ($C_8H_5N_3O_2$, M=175).

Phasis 2

The intermediate compound of formula IV obtained in the first step is used to prepare a photochromic compound having formula II wherein $R_4$ is H and $R_1$, $R_2$, and $R_3$ are equal to methyl groups, as follows:

1.4. $10^{-3}$ mole of a Fischer's base, i.e. 1,3,3 trimethyl-2-methylen indolin, dissolved in 10 ml of n-heptane and 2 ml of dry ethanol, are refluxed. At constant temperature (nearby 76° C.) 1.4 $10^{-3}$ mole of 5-nitroso 6-hydroxy-quinazolin as a suspension in 12 ml of dry ethanol, are slowly added during 2 hours.

The reaction mixture is maintained under reflux for 45 minutes. As the reaction is gradually developing, water is removed with ethanol by a Dean Stark Apparatus. Then 30 ml of ethanol are added up to a constant volume of solvent.

After passing the reaction mixture through a silica gel chromatographic column and removing the solvent, the solid residue is recrystallized in an appropriate mixture of apolar solvents such as petroleum ether, ether oxide, n-hexane, or benzene.

The product obtained is the indolino-spiro-oxazin compound of formula II, i.e. tri-methyl indolino-spiro-quinazolino-oxazin. The yield is about 50%, when the reaction solvent is a mixture of n-heptane and ethanol. Subsequent purification by recrystallization decreases the final yield to 40%.

Melting point F=169° C. ($C_{20}H_{18}N_4O$, M=330).

EXAMPLE II

Following the same synthesis route as in example 1 one obtains the compound of formula II wherein $R_1$ is $iC_3H_7$, $R_2=R_3=$methyl, $R_4=H$, $R_5=H$, starting from 5-nitroso 6-hydroxy-quinazolin and from the Fischer's base 1-isopropyl 2-methylene 3,3-dimethyl indolin.

Melting point =180° C. ($C_{22} H_{22} N_4 O$, M =358)

EXAMPLE III

Similarly one obtains the compound of formula II wherein $R_1$ is $CH_3$ as well as $R_2$ and $R_3$, $R_4$ is a methoxy group in the 5th position on the indolin ring and $R_5$ is H, starting from 5-nitroso 6-hydroxyquinazolin and from the Fisher's base 1,3,3 trimethyl 2 methylen 5 methoxy indolin.

Final compound: $C_{21}H_{20}N_4O_2$, Melting point MP=140° C.

EXAMPLE IV

The tri-methyl indolino-spiroquinazolino-oxazine obtained in example I is introduced in a polysiloxane varnish of the type described in French Patent FR 82 0440 at the proportion of 1% by weight. The varnish obtained is applied on ophtalmic lenses made of an organic material, then cured for two hours at 100° C. The thickness of the layers obtained is 2 microns. The percentage by weight of the photochromic compound in the cured layer is of the order of 5%.

The lenses thus coated are submitted to irradiation tests by means of an apparatus commercially known under the name of SUNTEST ORIGINAL HANAU under the following conditions:
Emitter: xenon source;
Energetic rays of 1000 W per square meter within the-range of wave lengths from 300 to 830 nm;
Lightness: 150 kilolux;
Room temperature: 40° C.

Photochromism under radiation is evaluated visually every two hours. The photochromic effect is shown to remain after 4 hours irradiation.

As comparative examples the same tests have been performed on varnishes prepared in the same way with the photochromic compounds of the prior art and it has been observed that:

1 With the trimethyl-indolino-spiro-naphto-oxazin of U.S. Pat. No. 3,578,602 the photochromic effect has disappeared after not more than a 2 hours irradiation.

2 With the trimethyl-indolino-spiro-quinolino-oxazin of U.S. Pat. No. 4,720,547 the photochromic effect is reduced at 2 hours irradiation and completely stopped before 4 hours irradiation.

Of course the invention is not at all limited by the particularities that have been specified in the preceding examples or by the details of the specific modes of implementation illustrating the invention. All sorts of variations can be used as regards the operating conditions as well as the nature and the proportions of the constituents and reactants while still remaining within the scope of the invention.

We claim:

1. A photochromic compound being an indolino-spiro-oxazine comprising an indolinic part attached to an oxazine part, said compound being of the formula:

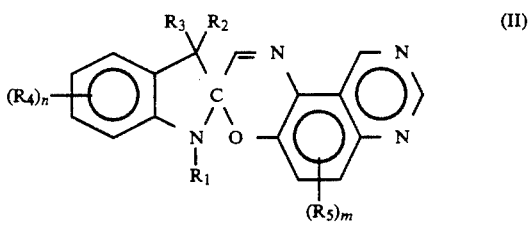

(II)

wherein:
n is 0 to 4;
m is 1 or 2;
$R_1$ represents:
 (i) alkyl of 1 to 16 carbon atoms;
 (ii) allyl, unsubstituted phenyl, or phenyl mono- or disubstituted by at least one alkyl of 1–6 carbon atoms and alkoxy of 1–6 carbon atoms; or
 (iii) cyclohexyl; or
 (iv) aliphatic hydrocarbon chain of 1–16 carbon atoms having at least one heteroatom interspersed in the chain, said heteroatom being N, O, or S;
$R_2$ and $R_3$ each independently represents a $C_{1-8}$-alkyl, unsubstituted phenyl, or phenyl mono- or disubstituted by at least one of $C_{1-4}$-alkyl and $C_{1-5}$-alkoxy, or $R_2$ and $R_3$ combined represent a cyclic ring of 6 to 8 carbon atoms including the 3-spirannic carbon of the indolinic heterocycle;

$R_4$ and $R_5$ each independently represents:
 (i) an amine function NR'R" wherein R' and R" each independently represents a hydrogen atom, alkyl of 1–6 carbon atoms, cycloalkyl of up to 6 carbon atoms or phenyl; or R' and R" combined represent cycloalkyl of up to 6 carbon atoms group optionally comprising one heteroatom; or
 (ii) R, OR, SR, COR or COOR wherein R represents a hydrogen atom, alkyl of 1 to 6 carbon atoms or phenyl; or
 (iii) a halogen atom, $C_{1-4}$-monohaloalkyl or $C_{1-4}$-polyhaloalkyl; or
 (iv) $NO_2$, CN, or SCN.

2. A photochromic compound according to claim 1, wherein $R_1$ is $C_{1-4}$-alkyl, phenyl or benzyl; $R_2$ and $R_3$ are each selected from $C_{1-5}$-alkyl groups, phenyl groups or are combined to form a cyclohexyl group; each of the $R_4$ groups is selected from the group consisting of hydrogen, $C_{1-2}$-alkyl, chlorine, fluorine, bromine, iodine, $C_{1-2}$-trihaloalkyl and $C_{1-5}$-alkoxy; and $R_5$ is a hydrogen atom, a $C_{1-4}$-alkoxy group, a tertiary amine or a halogen.

3. A photochromic compound according to claim 2, wherein $R_1$ is a $C_{1-4}$-alkyl; $R_2$ and $R_3$ each independently represents a methyl, ethyl, or phenyl group; $R_4$ is hydrogen atom, methyl, methoxy, chloro; $R_5$ is a hydrogen atom.

4. A photochromic compound according to claim 3, wherein $R_1$ is methyl or isopropyl; $R_2$ and $R_3$ are methyl groups; $R_4$ is H or $-OCH_3$.

5. A photochromic composition for optical lenses comprising at least one compound according to claim 1 in a photochromic amount.

6. A photochromic composition for optical lenses comprising at least compound according to claim 2 in a photochromic amount.

7. A photochromic compound according to claim 1, wherein n=1.

8. A photochromic compound according to claim 1, wherein n=2 and $R_4$ is present at the 4 and 5, 5 and 6, or 6 and 7 positions.

9. A photochromic compound according to claim 1, wherein $R_1$ is methyl, ethyl, n-propyl, isopropyl, or n-butyl.

10. A photochromic compound according to claim 1, wherein $R_1$ is benzyl or phenyl monosubstituted by alkyl or alkoxy having 1 to 6 carbon atoms.

11. A photochromic compound according to claim 1, wherein $R_1$ is a cyclohexyl group.

12. A photochromic compound according to claim 1, wherein $R_4$ and $R_5$ represent $CF_3$.

13. A photochromic compound according to claim 1, wherein the aliphatic hydrocarbon chain of $R_1$ contains an acid, ester or alcohol group.

14. A photochromic compound according to claim 1, wherein the halogen in $R_4$ and $R_5$ is Cl or Br.

15. A composition according to claim 5, wherein the compound is dissolved in a polymer, copolymer or a mixture of polymers in a suitable organic solvent.

16. A composition according to claim 15, wherein the compound is in combination with a polysiloxane varnish.

17. A lens comprising at least one of the compounds of claim 1.

18. A lens according to claim 17, wherein the compound is provided on the lens as a coating.

19. Photochromic compositions for optical lenses comprising at least one compound according to claim 1 in photochromic amount.

* * * * *

UNITED STATES PATENT AND TRADEMARK OFFICE
CERTIFICATE OF CORRECTION

PATENT NO. : 5,139,707
DATED : August 18, 1992
INVENTOR(S) : Robert Guglielmetti et al It is certified that error appears in the above-indentified patent and that said Letters Patent is hereby corrected as shown below:

On the title page, item [54], lines 1, 2 and 3, and in column 1, lines 1 and 2, in the title "SPIROQUINOXALINO" should read -- -SPIROQUINAZOLINE- --; "PHOTOCHROMATIC" should read --PHOTOCHROMIC--; and "METHODS" should read --METHOD--.

Signed and Sealed this

Fifth Day of April, 1994

Attest:

BRUCE LEHMAN

*Attesting Officer*     Commissioner of Patents and Trademarks